United States Patent [19]

Kuroda et al.

[11] Patent Number: 5,290,681
[45] Date of Patent: Mar. 1, 1994

[54] METHOD OF ASSAYING IMMUNIZATION STIMULATING ACTIVITY

[75] Inventors: Kazuhiko Kuroda, Yokohama; Hiroki Murakami, Fukuoka; Shuichi Hashizume, Yokohama, all of Japan

[73] Assignee: Morinaga & Co., Ltd., Tokyo, Japan

[21] Appl. No.: 842,262

[22] Filed: Feb. 27, 1992

[30] Foreign Application Priority Data

Mar. 8, 1991 [JP] Japan .................. 3-069273

[51] Int. Cl.$^5$ .................. G01N 33/574; G01N 33/53; G01N 33/567
[52] U.S. Cl. .................. 435/7.23; 435/7.24; 435/172.2; 435/70.1; 435/70.2; 435/70.21; 435/70.3; 435/240.23; 435/70.4; 436/63; 436/64; 436/547; 436/548; 530/388.15; 530/388.8
[58] Field of Search .................. 435/7.24, 70.1, 70.2, 435/70.21, 70.3, 172.2, 240.26, 240.27, 7.23, 240.23; 436/63, 64, 547, 548; 530/387.1, 388.1, 388.15, 388.8

[56] References Cited

U.S. PATENT DOCUMENTS 3,862,303 1/1975 Anderson .................. 424/12

FOREIGN PATENT DOCUMENTS 0454225 10/1991 European Pat. Off. .

OTHER PUBLICATIONS

Reading, C. L., et al. "Theory & Methods for Immunization in Culture and Monoclonal Antibody Production," Journal of Immunological Methods, 53, pp. 261-291, 1982.

Mond, J. J., et al., "Analysis of B Cell Activation Requirements with TNP-Conjugated Polyacrylamide Beads", Journal of Immunology, 123, pp. 239-245, 1979.

Power, et al. *Human Antibod. Hybridomas.* (1990) vol. 1, No. 1, pp. 34-41.

Kenneth Carroll, "In Vitro Immunization of Human Tonsilar Lymphocytes: Effects of PWM and rIL-6", Hybridoma, vol. 10, No. 2, Apr. 1991.

G. Kohler et al, "Continuous cultures of fused cells secreting antibody of predefined specificity", Nature, vol. 256, pp. 495-497, (1975) UK.

Ho et al, In Vitro Immunication of Human Lymphocytes, I. "Production of Human Monoclonal Antibodies Against Bombesin and Tetanus Toxoid", The J. of Immunol., vol. 135, No. 6, pp. 3831-3838 (1985) USA.

Teng et al, "Stragegies for Stable Human Monoclonal Antibody Production, Construction of Heteromyelomas, in Vitro Sensitization, and Molecular Cloning of Human Immunoglobulin Genes", ed. Engleman et al, Plenum Press, pp. 71-91 (1985) USA.

May-Kin Ho, "Production of Human Monoclonal Antibodies by In Vitro Immunization", ed. Strelkauskas (Marcel Dekker), pp. 23-38 (1987), USA.

Borrebaeck et al, "Human monoclonal antibodies produced by primary in vitro immunication of peripheral blood lymphocytes", Proc. Natl. Acad. Sci., vol. 85, pp. 3995-3999 (1988) USA.

M. Bieber et al, "In Vitro Sensitization for the Production of Human Monoclonal Antibodies", ed. Strelkauskas (Marcel Dekker), pp. 39-46, (1987) USA.

*Primary Examiner*—Toni R. Scheiner
*Attorney, Agent, or Firm*—Frishauf, Holtz, Goodman & Woodward

[57] ABSTRACT

A method of assaying immunization stimulating activity comprising (a) immunizing a lymphocyte in vitro by culturing the lymphocyte in contact with an immobilized antigen in a medium containing a test substance and (b) detecting an immunoglobulin, which is produced and secreted into the medium by the immunized lymphocyte and bound to the immobilized antigen, by counting the immunostained spots deposited in situ on the surface of the immobilized antigen.

5 Claims, No Drawings

METHOD OF ASSAYING IMMUNIZATION STIMULATING ACTIVITY

BACKGROUND OF THE INVENTION

1. Field of the Invention

This invention relates to a method for the extremely effective in vitro immunization of lymphocytes for the production of antibody specific to the antigen, as well as a method for the assay of immunization stimulating activity by applying a cell culture system.

2. Description of the Prior Art

Since Köhler and Milstein established, in 1975, a method for generating mouse hybridoma cell lines producing monoclonal antibodies in vitro (Nature 1975, 256, 495–497), innumerable monoclonal antibodies of mouse origin directed to various antigens have been developed and many of them are currently being employed for the in vitro diagnostic use such as serodiagnosis. Although human monoclonal antibodies can also be produced by applying the method of Köhler and Milstein and these antibodies of mouse and human origins are anticipated for the therapeutic use, no monoclonal antibody has ever employed in practical therapy.

It is a generally accepted concept that monoclonal antibodies of human origin are preferable for administration to humans than those of mouse origin. However, applications of human monoclonal antibodies to the clinical use have been hampered thus far partly due to the lack of effective methods for providing human lymphocytes immunized with the requested antigens, which are indispensable for the generation of hybridomas in concern, and partly due to the ethical reason that immunizations with favorable antigens in humans are not possible. In this context, extensive efforts are being made to establish efficient in vitro immunization methods to overcome the difficulties (J. Immunol. 1985, 135, 3831–3838; Human Hybridoma and Monoclonal Antibody, Plenum Press, 1985, pp. 71–91).

SUMMARY OF THE INVENTION

The present invention provides an established method for the antigen-specific and efficient in vitro immunization of lymphocytes, which can facilitate generation of hybridomas of human and animal origins producing antigen-specific monoclonal antibodies. In the course of this invention, a simple method for assaying immunization stimulating activity was developed.

According to an embodiment of the in vitro immunization method of the present invention, the method comprises immunizing a lymphocyte capable of specifically responding to an antigen, by culturing a lymphocyte in contact with an antigen in a medium containing an adjuvant and a lymphokine in the absence of a polyclonal activator.

According to another embodiment of the in vitro immunization method of the present invention, the method comprises immunizing a lymphocyte capable of specifically responding to an antigen, by culturing a lymphocyte in contact with an antigen in a medium containing an adjuvant and a lymphokine in the absence of a polyclonal activator, followed by immortalization of the immunized lymphocyte.

The method of assaying immunization activity according to the present invention comprises culturing a lymphocyte in contact with an antigen in a medium containing an adjuvant, a lymphokine and a test substance in the absence of a polyclonal activator, and detecting a immunoglobulin produced by the immunized lymphocyte.

The present invention is based on the findings that the lymphocyte can be efficiently immunized in vitro in the antigen-specific manner in the cultivation medium containing an adjuvant and lymphokine(s) in the absence of polyclonal activator. The immunized lymphocyte can be immortalized if desired. The highest efficiency of in vitro immunization can be achieved when both the adjuvant and lymphokine(s) in combination are included in the medium simultaneously. When the polyclonal activator is added to the above mixture, the immunization efficiency decreases significantly. The application is not limited to the lymphocytes from special tissues but any lymphocyte can be applied to the in vitro immunization of the present invention.

The lymphocyte immunized in vitro producing the antigen-specific monoclonal antibody can be immortalized either by hybridizing with cells or a proper lymphocytic line or by infecting with Epstein-Barr virus, which can facilitate the efficient production of the antigen-specific monoclonal antibody. Applications of human monoclonal antibodies have been hampered thus far due to the difficulties in achieving a specificity high enough to the desired target antigen, as well as its adequate production. The present invention opens promising possibilities in the wide applications of human monoclonal antibodies to the prevention, diagnosis, and therapy by facilitating the prompt and efficient production of desired antigen-specific monoclonal antibodies.

The method for the assay of immunization stimulating activity can facilitate exploration of various effective materials enhancing the immunization efficiency by measuring their effects on the immunization response during the culture of lymphocytes in the media containing the test materials in the presence of adjuvant, lymphokines, and antigen.

DESCRIPTION OF THE PREFERRED EMBODIMENTS

In the present invention, insoluble antigens are preferably employed, such as cancer cells of established lines and latex particles on which soluble antigens are adsorbed.

For the adjuvant, either muramyl dipeptide (MDP) or OK-432, which is available from Chugai Pharmaceutical Co., Ltd., Japan, is preferably used. MDP concentrations in the cultivation medium ranging 0.1–1000 $\mu$g/ml, and more preferably 0.5–50 $\mu$g/ml, are employed successfully. As for OK-432, effective concentrations in the cultivation medium are 25–25,000 ng/ml, and more preferably in the range of 50–10,000 ng/ml.

As for the lymphokine, at least one of the interleukins (ILs)-2 and -6 or their combination is used. The effective concentrations of ILs in the cultivation medium are; for IL-2, 1–1000 units/ml, and more preferably 2–500 units/ml; for IL-6, 1–1000 units/ml, and more preferably 2–500 units/ml. An extremely high efficiency of in vitro immunization can be achieved by the combined use of ILs-2 and -6.

Although the culture is successfully performed in the media such as Dulbecco's modified Eagle medium (DMEM), Ham's F12, RPMI 1640, RDF (a 2:1:1 mixture of RPMI 1640, DMEM and Ham's F12), and ERDF (RDF in which contents of amino acids and vitamins are enriched), the latter two media are preferred.

Fresh lymphocytes from any origin, such as peripheral blood, surgically dissected lymph node and spleen, can be successfully employed for the in vitro immunization according to the present method.

In this method for the in vitro immunization of lymphocytes, significant decreases in immunization efficiency are observed in the presence of a polyclonal activator, such as endotoxins, dextran sulfate and lectins, including phytohemagglutinin, pokeweed mitogen, concanavalin A etc., which are usually employed in the conventional methods. Accordingly, it is essentially required for the in vitro immunization of the present invention to employ cultivation media which are devoid of the polyclonal activator.

The in vitro immunization is performed during the course of culture for 4–10 days after a lymphocyte suspension in the culture medium containing an adjuvant and lymphokine(s) is added to the insoluble antigen, such as cancer cells and latex-bound antigen as described above.

The lymphocytes thus cultured for the in vitro immunization are harvested and, if necessary, immortalized either by hybridizing with cells of a proper lymphocytic line or by infecting with Epstein-Barr virus. By the immortalization, new cell lines which produce antigen-specific monoclonal antibodies infinitely can be established, facilitating the production of monoclonal antibodies. The in vitro immunization with human lymphocytes results in the generation of cell lines producing human monoclonal antibodies, however, those with animal lymphocytes result in the creation of cell lines producing animal monoclonal antibodies of the corresponding animal species used.

The assay of immunization stimulating activity can be performed by the in situ immunostaining of antibodies, which had been secreted from immunized lymphocytes and bound to the antigen, in wells of the cultivation vessel. The stimulating effect of the test material on immunization efficiency can be evaluated in terms of difference in the number of immunostained spots of antibodies bound to the coated antigen during the cultivation of lymphocytes in the presence and absence of the test material. The present invention is detailed below with examples.

EXAMPLES

Example 1

Effects of adjuvants and lymphokines on the in vitro immunization of lymphocytes are shown.

The in vitro immunization of lymphocytes with antigen cells was performed as described below. Cells of A549 line (a human lung carcinoma cell line, ATCC CCL-185) suspended in the ERDF medium containing 10% fetal calf serum (FCS) at a density of $1 \times 10^4$ cells/ml was dispensed in 1 ml aliquots to a 24-well plate and cultured for 36 h at 37° C. The normal lymphocytes adjusted to a density of $2 \times 10^6$ cells/ml, which had been prepared by the fractionation of peripheral blood from a healthy volunteer with Ficoll-Paque (available from Pharmacia LKB Biotechnology AB, Upsala, Sweden) followed by four times washing with ERDF medium, was added in 0.5 ml aliquot to the above culture of A549 cells in the well. At the same time, MDP, OK-432, ILs-2 and -6 (available from Genzyme Corp., MA, U.S.A.) in various combinations of concentrations, including a combination at 250 ng/ml, 10 μg/ml, 100 units/ml, 10 units/ml, respectively, were included in the culture. The cultivation was continued for 4 days at 37° C.

The immunization stimulating activities of the adjuvants and lymphokines were assayed in situ with the lymphocytes thus cultured. After the removal of supernatant medium together with lymphocyte cells from the above described culture, A549 cells adhered to the well were fixed with 0.06% glutaraldehyde for 15 min at 4° C. following three times washing with ERDF. The wells containing immobilized antigen cells, to which antigen-specific antibodies secreted by the immunized lymphocytes by the immunized lymphocytes had been bound, were further washed for three times with a phosphate-buffered saline (PBS) containing 0.05% Tween 20, followed by blocking with 0.2% gelatin-0.5% Bovine serum albumin in PBS for 2 h at 37° C. After discarding the blocking solution, a mixture of biotinylated anti-human IgG and biotinylated anti-human IgM was added and incubated for 1 h at 37° C. After washing the wells extensively, the avidin-peroxidase conjugate was added and reaction proceeded for 1 h at 37° C., washed, and finally the spots of antibodies bound to the antigen cells were visualized by the deposition of colored materials formed by the activity of peroxidase using 3,3'-diaminobenzidine (DAB) as the substrate. The immunization stimulating activities of adjuvants as well as those of ILs were determined by counting microscopically the number of stained spots in each well, i.e., the number of lymphocytes producing the antigen-specific immunoglobulins.

The effects of adjuvants and lymphokines on the in vitro immunization are summarized in Tables 1 and 2.

TABLE 1

Effects of adjuvants and lymphokines on in vitro immunization (experimental set-1).

| Lymphocyte | OK-432 | MDP | IL-2 | IL-6 | Number of immunostained spot |
|---|---|---|---|---|---|
| − | − | − | − | − | 0 |
| + | − | − | − | − | 1 ± 1 |
| + | + | − | − | − | 5 ± 1 |
| + | + | − | + | − | 15 ± 2 |
| + | + | − | − | + | 8 ± 2 |
| + | + | − | + | + | 14 ± 2 |
| + | − | + | + | + | 26 ± 5 |

TABLE 2

Effects of adjuvants and lymphokines on in vitro immunization (experimental set-2).

| Lymphocyte | OK-432 | MDP | IL-2 | IL-6 | Number of immunostained spot |
|---|---|---|---|---|---|
| + | − | − | − | − | 0 |
| + | − | − | + | − | 9 ± 5 |
| + | − | − | − | + | 2 ± 1 |
| + | − | − | + | + | 9 ± 4 |
| + | + | − | + | + | 14 ± 3 |
| + | − | + | + | + | 22 ± 5 |

Tables 1 and 2 show that the addition of an adjuvant and a lymphokine(s) in combination is much more effective than each independent addition of the additives, especially in the combination of MDP, IL-2 and IL-6, for the occurrence of lymphocytes producing antibodies reactive to A549 cells.

Example 2

A similar experiment as Example 1 was performed with the lymphocytes from lymph nodes of two cancer patients, as well as those from peripheral blood of three healthy volunteers.

TABLE 3

In vitro immunization with lymphocytes from different tissues.

| Origin of lymphocyte | Number of immunostained spot | | |
|---|---|---|---|
| | No addition | OK-432 + IL-2 + IL-6 added | MDP + IL-2 + IL-6 added |
| Lymph node | 0 | 30 ± 4 | 26 ± 3 |
| 2 | 1 ± 0 | 14 ± 2 | 24 ± 2 |
| Peripheral blood | | | |
| 1 | 0 | 20 ± 5 | 52 ± 5 |
| 2 | 0 | 14 ± 5 | 26 ± 9 |
| 3 | 0 | 9 ± 4 | 18 ± 2 |

As shown in Table 3, no significant difference in the invitro immunization efficiency can be observed between the lymphocytes from lymph nodes and those from peripheral blood, indicating that lymphocytes from any tissue may be equally applicable for the in vitro immunization of the present invention.

Example 3

Effects of polyclonal activators such as lectins and lipopolysaccharide on the in vitro immunization were examined. The experimental conditions were the same as those of Example 1 except that 1% of pokeweed nitrogen (PWM) or 25 µg/ml of lipopolysaccharide (LPS) was included in the cultivation medium.

TABLE 4

Effects of polyclonal activators on in vitro immunization.

| Addition | | | | Number of immunostained spot |
|---|---|---|---|---|
| PWM | LPS | OK-4332 + IL-2 IL-6 | MDP + IL-2 IL-6 | |
| − | − | − | − | 0 |
| + | − | − | − | 1 ± 0 |
| − | + | − | − | 7 ± 2 |
| + | + | − | − | 4 ± 1 |
| − | − | + | − | 14 ± 3 |
| − | − | − | + | 22 ± 5 |
| + | + | + | − | 5 ± 0 |
| + | + | − | + | 6 ± 1 |

The results shown in Table 4 indicate that the polyclonal activators significantly inhibit the present in vitro immunization, through these activators are generally required for the conventional in vitro immunization methods.

Example 4

This example represents that the efficient generation of human hybridomas secreting antigen-specific antibodies into the cultivation media can be achieved by the immortalization of the lymphocytes which have been immunized in vitro according to the present method.

Lymphocytes from peripheral blood of a healthy volunteer were cultivated in a medium containing MDP, IL-2 and IL-6 in the presence of A549 cells as the antigen. The lymphocytes thus immunized were collected and hybridized by the conventional method employing polyethylene glycol with cells of RF-S1 (deposited in Fermentation Research Institute under FERM BP-3751) which is a lymphocytic mutant cell line derived from myelomas of human and mouse origins. The lymphocytes after the hybridization with RF-S1 cells were dispensed and cultured in 96-well plates. The spent media were assayed for antigen-specific antibodies by an enzyme-linked immunosorbent assay as below. The spent media dispensed to the wells of a 96-well plate, in which A549 cells grown to confluency had been fixed with glutaraldehyde and blocked in the same manner as detailed in Example 1, were incubated for 1 h at 37° C. followed by another incubation with avidine-peroxidase conjugate. The amount of immunoglobulins bound to the immobile phase were determined by measuring the bound peroxidase activity photometrically using 2,2′-azino-bis(3-ethylbenzothiazolin-6-sulfonic acid diammonium salt (ABTS) as the substrate. The wells showing positive color developments, i.e., those containing antibodies specifically reactive with A549 antigen were counted.

TABLE 5

Occurrence of antibodies specific to A549 cells in the spent media after cultivation of hybridomas generated by the hybridization of in vitro immunized lymphocytes and RF-S1 cells.

| Experiment | In vitro immunization | Wells plated | Wells with cell growth | Wells with reactive antibody |
|---|---|---|---|---|
| 1 | − | 192 | 192 | 0 |
| | + | 192 | 192 | 1 |
| 2 | − | 96 | 96 | 0 |
| | + | 96 | 68 | 1 |
| 3 | − | 192 | 100 | 0 |
| | + | 288 | 86 | 2 |

The results shown in Table 5 indicate that significantly high rates in the generation of hybridomas producing antigen-specific monoclonal antibodies can be attained by the present in vitro immunization method.

What is claimed is:

1. A method of assaying immunization stimulating activity comprising
   (a) immunizing a lymphocyte in vitro by culturing the lymphocyte in contact with immobilized cancer cells in a medium containing an adjuvant, a lymphokine and a test substance in the absence of a polyclonal actinator, said test substance not being said adjuvant or said lymphokine,
   (b) adding labeled anti-immunoglobulin antibody and
   (c) detecting an immunoglobulin, which is produced and secreted into the medium by the immunized lymphocyte and bound to the immobilized cancer cell, by counting immunostained spots deposited in situ on the surface of the immobilized cancer cell.

2. The method according to claim 1, wherein said lymphocyte is a lymphocyte originating from blood, lymph nodes or a spleen.

3. The method according to claim 2, wherein the medium is selected from the group consisting of Dulbecco's modified Eagle medium; Ham's F12; RPMI 1640; a 2:1:1 mixture of RPMI 1640, Dulbecco's modified Eagle medium and Ham's F12; and ERDF.

4. The method according to claim 1, wherein the cancer cells are cells of a human lung carcinoma cell line and the medium is ERDF.

5. The method according to claim 1, wherein the lymphokine is selected from the group consisting of interlukin-2, interlukin-6 and a combination thereof; the lymphokine is in a concentration in the medium of 1 to 1000 units/ml; and the adjuvant is selected from the group consisting of muramyl dipeptide in a concentration of 0.1 to 1000 µg/ml and OK-432 in a concentration of 25 to 25,000 ng/ml.

* * * * *